(12) United States Patent
O'Lenick, Jr.

(10) Patent No.: US 6,346,648 B1
(45) Date of Patent: Feb. 12, 2002

(54) AMPHOTERIC SURFACTANTS BASED UPON EPOXY SUCCINIC ACID

(75) Inventor: Anthony J. O'Lenick, Jr., Dacula, GA (US)

(73) Assignee: Applied Carbo Chemicals INC, East Lansing, MI (US)

( * ) Notice: Subject to any disclaimer, the term of this patent is extended or adjusted under 35 U.S.C. 154(b) by 0 days.

(21) Appl. No.: 09/493,172

(22) Filed: Jan. 28, 2000

(51) Int. Cl.$^7$ ............................................. C07C 229/16
(52) U.S. Cl. ....................... 562/568; 252/8.63; 510/434; 510/479; 510/480; 516/15; 516/67; 562/567; 562/571
(58) Field of Search ........................... 516/67; 510/434, 510/479, 480; 252/8.63; 564/103, 108; 562/567, 571, 568

(56) References Cited

U.S. PATENT DOCUMENTS

| | | | | |
|---|---|---|---|---|
| 2,097,864 A | * | 11/1937 | Platz et al. | 562/567 X |
| 2,183,853 A | * | 12/1939 | Haussmann et al. | 562/567 X |
| 2,712,545 A | * | 7/1955 | Bersworth | 562/571 X |
| 2,953,526 A | * | 9/1960 | Bergman et al. | 252/8.63 |
| 2,988,554 A | * | 6/1961 | Batzer et al. | 564/103 X |
| 3,142,568 A | * | 7/1964 | Nottorf | 516/67 X |
| 3,497,556 A | * | 2/1970 | Lanner et al. | 252/8.63 X |
| 3,929,874 A | * | 12/1975 | Beermann et al. | 562/568 X |
| 4,065,475 A | | 12/1977 | Hosri et al. | |
| 4,214,102 A | * | 7/1980 | Leenders | 510/479 X |
| 4,253,974 A | * | 3/1981 | Valcho et al. | 516/67 X |
| 5,608,089 A | | 3/1997 | Sato et al. | 549/531 |
| 5,846,925 A | * | 12/1998 | Wilson et al. | 510/434 X |
| 5,905,160 A | * | 5/1999 | Shimomura et al. | 562/567 X |
| 5,977,053 A | * | 11/1999 | Groth et al. | 510/480 |
| 6,063,302 A | * | 5/2000 | Asakawa et al. | 562/571 X |

FOREIGN PATENT DOCUMENTS

JP 49-30316 * 3/1974 ................. 562/568

* cited by examiner

Primary Examiner—Richard D. Lovering

(57) ABSTRACT

The present invention deals with novel compounds their applications and a process their preparation. The compounds are novel amphoteric surfactants that contain a hydroxyl group and two carboxylic groups per hydroxyl group. The compounds have a unique structure, having multiple carboxyl groups on each amino group. The utility for these novel polymers is as softening, anti-tangle, and conditioning agents for use in personal care, textile and related applications.

9 Claims, No Drawings

AMPHOTERIC SURFACTANTS BASED UPON EPOXY SUCCINIC ACID

1. FIELD OF THE INVENTION

The present invention deals with novel compounds, their applications and a process their preparation. The compounds are novel amphoteric surfactants that contain a hydroxyl group and two carboxylic groups per hydroxyl group. The compounds have a unique structure, having multiple carboxyl groups on each amino group. The utility for these novel polymers is as softening, anti-tangle, and conditioning agents for use in personal care, textile and related applications. The properties of these novel amphoteric polymeric compositions which makes them well suited for these applications is the fact that they are substantive to fibers, hair and skin and also very mild to the skin and eyes.

2. DESCRIPTION OF THE ARTS AND PRACTICES

Aminocarboxylic amphoteric surfactants have been known and used commercially for many years. Perhaps the most important early patent on the production of these materials is U.S. Pat. No. 2,195,974 to Reppe et al. The patent, issued in May 1936 and assigned to I. G. Farben, discloses the reaction of acrylic acid, methacrylic acid and ammonia or organic amines at temperatures at which amides do not form. The patent described many reaction conditions in addition many solvents were described ranging from water to other protic solvents. Reppe also describes many so-called "acrylic sources", which are suitable as raw materials for preparation of this class of amphoteric surfactants.

The surfactant properties of aminocarboxylic acids and salts are likewise well known to those skilled in the art. Over the years, these compounds have been found to have limited usefulness as foaming agents and detergents in some applications. The compounds have not enjoyed wider use in other applications, due to the fact the prior art compounds lack compatibility with anionic surface active agents, are not mild when applied to the eye and skin U.S. Pat. No. 3,417,136 issued to Hovden Dec. 17, 1968, attempts to develop a product with increased water solubility by incorporating an ether function into the molecule. Hovden states prior to his invention, the known aminocarboxylic acid surfactant compounds have a lesser water solubility than is desired in some applications. Further, he states many of these compounds do not have as great a wetting power as might be desired for certain applications. This is also a function of water solubility.

While Hovden's invention solved the difficulty of obtaining a series of products that are more water soluble and have improved wetting properties, it remained a problem to produce products with the desired anionic compatibility and mildness and electrolyte compatibility.

OBJECT OF THE INVENTION

It is the object of this invention to produce novel amphoteric compounds that have improved are highly substantive to hair, skin and fibers, have low irritation properties when placed on the skin or in the eyes, and are compatible with anionic surfactants. This improved performance relates to the fact that the products of this invention (a) contain fatty amino groups and (b) contain a poly carboxy functionality which results amphoterics with unique solubility, and emulsification properties in a variety of solvents. These materials also provide stable copious foam and much improved detergency properties over traditional amino proprionates.

Another object of the invention is to provide a novel class of amphoteric compounds that exhibit outstanding surface-active properties.

Still another object of the invention is a process for the treatment of skin, hair and fibers with an effective conditioning amount of the compounds of the invention.

Other objects of the invention will become clear from the disclosure.

THE INVENTION

The compounds of the present invention are poly-carboxy containing amphoteric surfactants. They compounds of the present invention conform to the following structure;

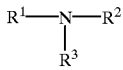

$R^1$ is selected from the group consisting of alkyl having from 6 to 20 carbon atoms and

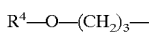

$R^4$ is alkyl having from 6 to 20 carbon atoms;
$R^2$ is

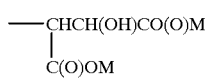

M is a cation needed for charge balance and is selected from the group consisting of Na, K, Li and H;
$R^3$ is selected from the group consisting of H and

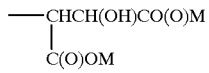

The compounds of the present invention are multi-carboxylates. In one instance a di carboxylate that has a secondary amine present. Typical of this type of compound is as follows:

In another preferred instance they are tetra carboxylates that have a tertiary amine present.

In this latter case the tetra carboxylate results in an amphoteric surfactant that is not sensitive to Ca ion. Standard amphoterics conform to the following structure:

These compounds have only two carboxyl groups that branch at nitrogen, lack the hydroxy group and consequently have poor hard water tolerance.

PREFERRED EMBODIMENTS

By properly selecting the number of carbon atoms in the alkyl or alkyl ether group a product that has the proper balance between water-soluble and oil soluble groups is attained.

In a preferred embodiment $R^1$ is of alkyl having from 6 to 20 carbon atoms

In a preferred embodiment $R^1$ is $R^4$—O—$(CH_2)_3$—.

In a preferred embodiment $R^1$ is M is H.

In a preferred embodiment $R^1$ is M is Na.

In a preferred embodiment $R^1$ is M is K.

In a preferred embodiment $R^1$ is M is Li.

In a preferred embodiment $R^3$ is H.

In a preferred embodiment $R^3$ is

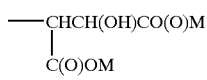

In a preferred embodiment $R^1$ is of alkyl having 6 carbon atoms.

In a preferred embodiment $R^1$ is of alkyl having 8 carbon atoms.

In a preferred embodiment $R^1$ is of alkyl having 10 carbon atoms.

In a preferred embodiment $R^1$ is of alkyl having 12 carbon atoms.

In a preferred embodiment $R^1$ is of alkyl having 14 carbon atoms.

In a preferred embodiment $R^1$ is of alkyl having 16 carbon atoms.

In a preferred embodiment $R^1$ is of alkyl having 18 carbon atoms.

In a preferred embodiment $R^1$ is of alkyl having 20 carbon atoms.

In a preferred embodiment $R^4$ is of alkyl having 6 carbon atoms.

In a preferred embodiment $R^4$ is of alkyl having 8 carbon atoms.

In a preferred embodiment $R^4$ is of alkyl having 10 carbon atoms.

In a preferred embodiment $R^4$ is of alkyl having 12 carbon atoms.

In a preferred embodiment $R^4$ is of alkyl having 14 carbon atoms.

In a preferred embodiment $R^4$ is of alkyl having 16 carbon atoms.

In a preferred embodiment $R^4$ is of alkyl having 18 carbon atoms.

In a preferred embodiment $R^4$ is of alkyl having 20 carbon atoms.

EXAMPLES

Raw Materials

A. Amines

1. Alkyl Amines $R^1$ is of alkyl having from 6 to 20 carbon atoms

| Example | $R^1$ |
|---|---|
| 1 | $C_6H_{13}$ |
| 2 | $C_8H_{17}$ |
| 3 | $C_{10}H_{21}$ |
| 4 | $C_{12}H_{25}$ |

-continued

| Example | $R^1$ |
|---|---|
| 5 | $C_{14}H_{29}$ |
| 6 | $C_{16}H_{33}$ |
| 7 | $C_{18}H_{37}$ |
| 8 | $C_{20}H_{41}$ |

2. Alkyl Ether Amines

| Example | $R^4$ |
|---|---|
| 9 | $C_6H_{13}$ |
| 10 | $C_8H_{17}$ |
| 11 | $C_{10}H_{21}$ |
| 12 | $C_{12}H_{25}$ |
| 13 | $C_{14}H_{29}$ |
| 14 | $C_{16}H_{33}$ |
| 15 | $C_{18}H_{37}$ |
| 16 | $C_{20}H_{41}$ |

B. Epoxy Succinate (Disodium cis-epoxysuccinate):

A solution of 23.2g (0.2 mole) of maleic acid in 15 ml distilled water was added to a 200 ml beaker. A solution of 12g (0.3 mole) of sodium hydroxide in 10 ml water, 0.66g (0.02 mole) of sodium tungstate were added in the above mixture. The hot solution (heated by neutralization) was brought to a temperature below 65C. A standard pH electrode was inserted into the solution and 24.5 ml (0.24 mole, 30%) hydrogen peroxide was added all at once.

The reaction began to be observed at 65° C. the reaction is strongly exothermic. The temperature was held at about 65–70° C. for 45 min. During the reaction period the pH fell from about 5.5 to 2. A concentrated sodium hydroxide solution was added dropwise to maintain the pH about 4.5–5.

After an additional hour at 65° C., the reaction mixture was cooled a little bit and poured it into 250 ml acetone with stirring. About 35g disodium cis-epoxysuccinate was precipitated. (Yield about 100%)

Amphoteric Preparation

GENERAL PROCEDURE

Example 17–32

Mono Functional

In a suitable three neck flask equipped with agitation and thermometer, is added 1000 grams of water, 182.0 grams of disodium cis-epoxysuccinate. Next, the specified amount of the specified amine reactant (examples 1–16) is added. The reaction mass will thicken as heat is applied. At about 80–90 C the viscosity thins out. Hold at this temperature 5 to 9 hours. The reaction is complete when the tertiary amine concentration reaches at least 97% of theoretical. Add enough base to neutralize the product to a pH of 7 to 8. Addition is exothermic and is controlled by submersion of the flask into a cooling bath. The product is now present in aqueous solution and can be used without purification or can be dried down in a roto-evaporator if desired.

| Example | Amine Example | Grams |
|---------|---------------|-------|
| 17 | 1 | 101.0 |
| 18 | 2 | 129.0 |
| 19 | 3 | 157.0 |
| 20 | 4 | 185.0 |
| 21 | 5 | 213.0 |
| 22 | 6 | 247.0 |
| 23 | 7 | 269.0 |
| 24 | 8 | 297.0 |
| 25 | 9 | 147.0 |
| 26 | 10 | 175.0 |
| 27 | 11 | 203.0 |
| 28 | 12 | 231.0 |
| 29 | 13 | 259.0 |
| 30 | 14 | 293.0 |
| 31 | 15 | 315.0 |
| 32 | 16 | 343.0 |

Example 33–48

Di Functional

In a suitable three neck flask equipped with agitation and thermometer, is added 1000 grams of water, 364.0 grams of disodium cis-epoxysuccinate. Next, the specified amount of the specified amine reactant (examples 1–16) is added. The reaction mass will thicken as heat is applied. At about 80–90 C the viscosity thins out. Hold at this temperature 5 to 9 hours. The reaction is complete when the tertiary amine concentration reaches at least 97% of theoretical. Add enough base to neutralize the product to a pH of 7 to 8. Addition is exothermic and is controlled by submersion of the flask into a cooling bath. The product is now present in aqueous solution and can be used without purification or can be dried down in a roto-evaporator if desired.

| Example | Amine Example | Grams |
|---------|---------------|-------|
| 33 | 1 | 101.0 |
| 34 | 2 | 129.0 |
| 35 | 3 | 157.0 |
| 36 | 4 | 185.0 |
| 37 | 5 | 213.0 |
| 38 | 6 | 247.0 |
| 39 | 7 | 269.0 |
| 40 | 8 | 297.0 |
| 41 | 9 | 147.0 |
| 42 | 10 | 175.0 |
| 43 | 11 | 203.0 |
| 44 | 12 | 231.0 |
| 45 | 13 | 259.0 |
| 46 | 14 | 293.0 |
| 47 | 15 | 315.0 |
| 48 | 16 | 343.0 |

APPLICATIONS EXAMPLES

The amphoteric compounds of this invention can be formulated into softeners that are applied directly in aqueous solution by themselves or formulated with anionic, nonionic or amphoteric surfactants and builders to prepare finished conditioner/detergent systems. The level of composition of the present invention is typically used at a weight ratio to water of about 1:10:000 to 1:20 to soften fabric.

Conditioners and Shampoos using the compositions employ it at 2% to 30% by weight. Anionic surfactants include laurel and stearyl sulfate as well as alkylbenzene sulfonates, Preferably the sodium salts. Nonionic surfactants include alkylalkoxylates typically having from 10 to 20 carbon atoms in the alkyl group and from 1 to 10 alkylene oxide units (preferably ethylene). Builders include the phosphates STPP and SPP as well as aluminosilicates.

Wet Comb out Test

A laboratory test is conducted to screen the wet comb properties of a representative member of the family of novel compositions. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate.

Subsequently, the swatch is washed under running tap water. The hair is then squeezed out and while still damp dipped into a 200-ml solution of 0.2% active product. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12–14 seconds.

Rinse Conditioner (Wet Comb Out Test)

| Product | Time in Seconds |
|---------|-----------------|
| Example #33 | 11 |
| Example #47 | 13 |
| Stearyldimethylbenzyl ammonium chloride | 12 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A compound conforming to the following structure:

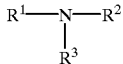

$R^1$ is $R^4$—O—$(CH_2)_3$—

$R^4$ is alkyl having from 6 to 20 carbon atoms;

$R^2$ is

M is a cation selected from the group consisting of Na, K, Li and H;

$R^3$ is selected from the group consisting of H and

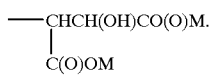

2. A compound of claim 1 wherein $R^4$ is $C_6H_{13}$.
3. A compound of claim 1 wherein $R^4$ is $C_8H_{17}$.
4. A compound of claim 1 wherein $R^4$ is $C_{10}H_{21}$.
5. A compound of claim 1 wherein $R^4$ is $C_{12}H_{25}$.
6. A compound of claim 1 wherein $R^4$ is $C_{14}H_{29}$.
7. A compound of claim 1 wherein $R^4$ is $C_{16}H_{33}$.
8. A compound of claim 1 wherein $R^4$ is $C_{18}H_{37}$.
9. A compound of claim 1 wherein $R^4$ is $C_{20}H_{41}$.

* * * * *